(12) United States Patent
Kim et al.

(10) Patent No.: US 12,400,408 B2
(45) Date of Patent: Aug. 26, 2025

(54) EXTENDED REALITY COMMUNICATIONS ENVIRONMENT

(71) Applicant: Veyond Metaverse Inc., Fremont, CA (US)

(72) Inventors: Kyeong Baek Kim, San Jose, CA (US); Joon Chung, Toronto (CA); William H. Chapman, Jr., Boca Raton, FL (US); Jafer Mujtaba Kamoonpuri, Vaughan (CA); Beomseok Gwak, Seoul (KR); Adam Yongsuk Choe, Castro Valley, CA (US); Mohsen Rostami, Toronto (CA); Han Yu Liu, Mississauga (CA); Pratik Pradhan, Mississauga (CA); Joshua Dongwoo Choe, Castro Valley, CA (US)

(73) Assignee: Veyond Metaverse Inc., Fremont, CA (US)

(*) Notice: Subject to any disclaimer, the term of this patent is extended or adjusted under 35 U.S.C. 154(b) by 0 days.

(21) Appl. No.: 18/493,344

(22) Filed: Oct. 24, 2023

(65) Prior Publication Data

US 2024/0135661 A1 Apr. 25, 2024
US 2024/0233290 A9 Jul. 11, 2024

Related U.S. Application Data

(60) Provisional application No. 63/380,740, filed on Oct. 24, 2022.

(51) Int. Cl.
*G06T 19/00* (2011.01)
*G06F 3/01* (2006.01)
(Continued)

(52) U.S. Cl.
CPC ............ *G06T 19/006* (2013.01); *G06F 3/014* (2013.01); *G06F 3/016* (2013.01); *G06F 3/017* (2013.01);
(Continued)

(58) Field of Classification Search
CPC ............ G06T 19/006; G06T 2219/024; G06T 2207/30196; G06F 3/014; G06F 3/016;
(Continued)

(56) References Cited

U.S. PATENT DOCUMENTS 9,298,884 B1 3/2016 Ahmad
10,432,913 B2 10/2019 Shokri et al.
(Continued)

FOREIGN PATENT DOCUMENTS

CN 106527738 A * 3/2017 ............ G06F 3/014
JP 2012015661 A * 1/2012

*Primary Examiner* — Douglas Wilson
(74) *Attorney, Agent, or Firm* — Squire Patent Consulting & IP Law LLC; Brendan E. Squire

(57) ABSTRACT

A extended reality communication system, methods, apparatus, and computer program product are disclosed. The communication system provides for remote real-time communication between a proctor and an operator, where the operator is performing tasks on a local work object, such as a patient. The system incorporates a combination of haptic, virtual keyboard, VR, XR, and audio inputs to provide communication of instructions between the proctor and the operator that are projected as a holographic image in a field of view on the patient. The system includes a proctor station and an operator station communicatively coupled with one or more servers.

5 Claims, 16 Drawing Sheets

(51) Int. Cl.
  *G06F 40/58* (2020.01)
  *H04N 13/243* (2018.01)
  *H04N 13/271* (2018.01)
  *A61B 5/00* (2006.01)
  *G16H 80/00* (2018.01)

(52) U.S. Cl.
  CPC ........... *G06F 40/58* (2020.01); *H04N 13/243* (2018.05); *H04N 13/271* (2018.05); *A61B 5/745* (2013.01); *G06F 3/011* (2013.01); *G06T 2207/30196* (2013.01); *G06T 2219/024* (2013.01); *G16H 80/00* (2018.01)

(58) Field of Classification Search
  CPC .......... G06F 3/017; G06F 40/58; G06F 3/011; H04N 13/243; H04N 13/271; A61B 5/745; G16H 80/00
  See application file for complete search history.

(56) References Cited

U.S. PATENT DOCUMENTS

| | | | |
|---|---|---|---|
| 2012/0046933 A1* | 2/2012 | Frei | G10L 13/00 |
| | | | 704/2 |
| 2018/0322702 A1* | 11/2018 | Djajadiningrat | G16H 80/00 |
| 2020/0409461 A1* | 12/2020 | Crowther | G09B 5/02 |
| 2021/0271937 A1* | 9/2021 | Zhang | G06T 7/30 |
| 2022/0110684 A1* | 4/2022 | Mensink | A61B 34/20 |
| 2024/0112414 A1* | 4/2024 | Wanbo | G06T 7/13 |

\* cited by examiner

System Flow
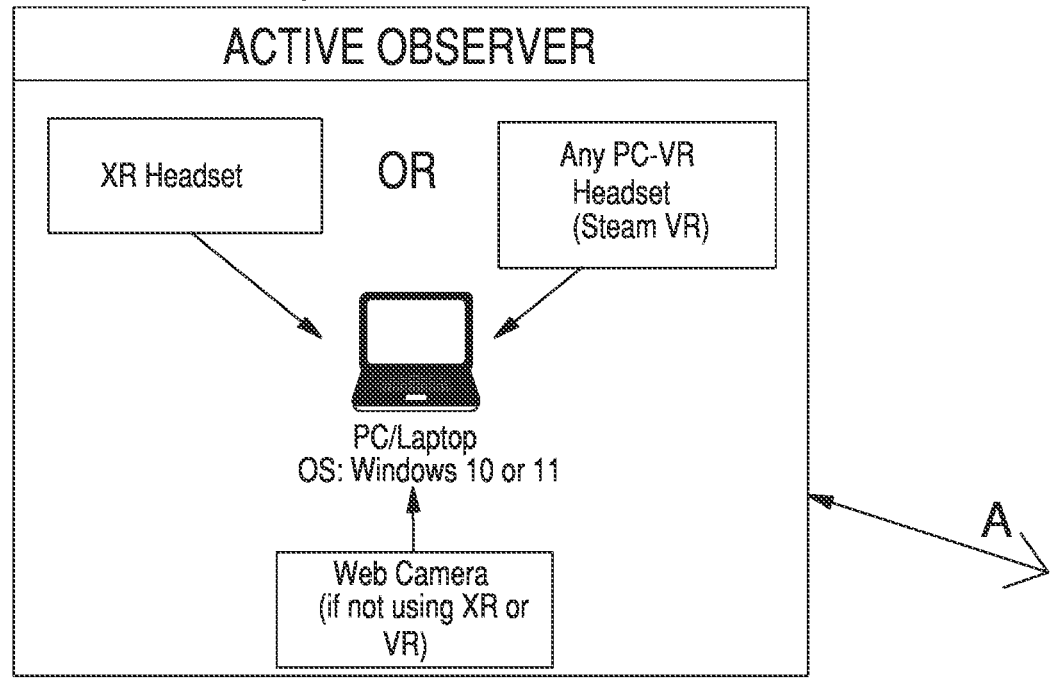
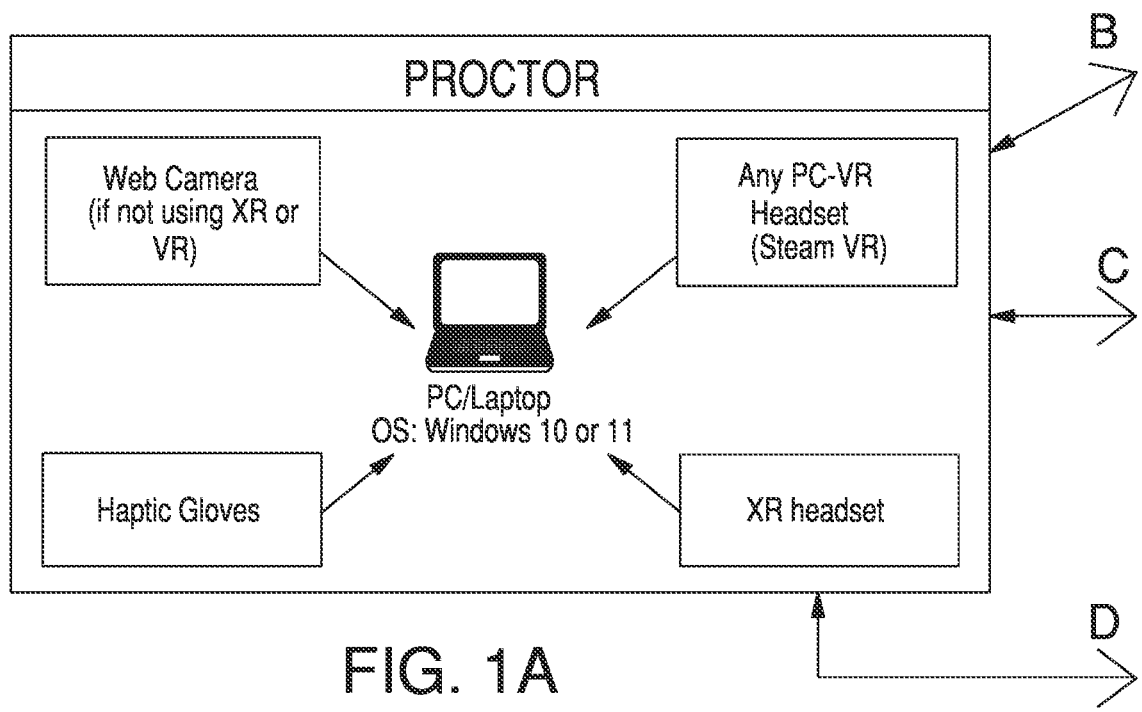
FIG. 1A

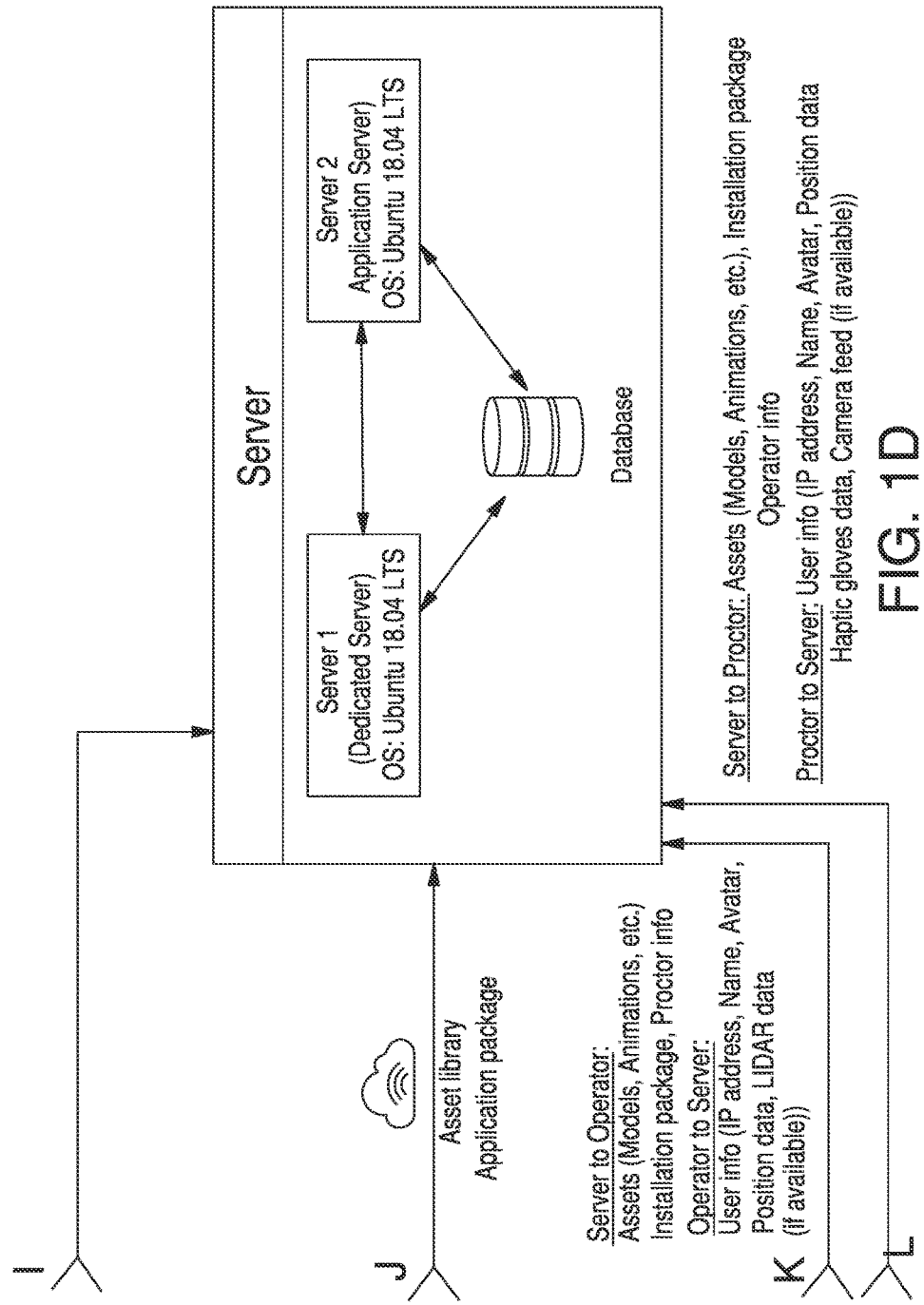

|  | Real Situation Perspectives | | | |
| --- | --- | --- | --- | --- |
|  | Operators | Operator Assistants | Proctors | Observers |
| Objects | AR or XR | AR or XR | VR/with Controller or Haptic Glove/ Desktop | VR/Desktop |
| Patient | Real | Real | Virtual (real-time update from Operator side fixed LiDAR + RGB cameras) | |
| Surroundings | Real | Real | Virtual (prebuilt, stationary) | |
| Instruments | Real + Virtual (from Proctor side) | Real + Virtual (from Proctor side) | Virtual (LiDAR + RGB feeds/images from Operator side + Virtual (Pure Virtual) | |
| CT/MTI/EKG/ Zoom Camera/... | Real Display or Virtual (Gesture or Protor control) | Real Display or Virtual (Gesture or Voice control) | Virtual | |
| Operators | Self | Real | LiDAR Hologram | |
| Assistants | Real | Self | LiDAR Hologram | |
| Proctors | Avatar | Avatar | Self | Avatar |
| Observers | Avatar (Optional) | Avatar (Optional) | Avatar (Optional) | Self |
| Issues | Pre-calibrated LiDAR + RGB cameras Coordinate sync | | | |

Description of the perspective viewed by all parties involved in the basic communication product.

FIG. 3A

| XR Training/ Planning Perspectives | | | |
|---|---|---|---|
| Operators | Operator Assistants | Proctors | Observers |
| AR or XR | AR or XR | VR/with Controller or Haptic Glove/ Desktop | VR/Desktop |
| Virtual | Virtual | Virtual (real-time update from Operator side fixed LiDAR + RGB cameras) | |
| Real/Green Room | Real/Green Room | Virtual (prebuilt, stationary) | |
| Real / Virtual (from Proctor side) | Real / Virtual (from Proctor side) | Virtual (LiDAR + RGB feeds/images from Operator side + Virtual (Pure Virtual) | |
| Virtual | Virtual | Virtual | |
| Self | Real/ Avatar | LiDAR Hologram/ Avatar | |
| Real/ Avatar | Self | LiDAR Hologram/ Avatar | |
| Avatar | Avatar | Self | Avatar |
| Avatar (Optional) | Avatar (Optional) | Avatar (Optional) | Self |
| Pre-calibrated LiDAR + RGB cameras Coordinate sync | | | |

Description of the perspective viewed by all parties involved in the basic communication product (contd.).

FIG. 3B

| VR Training Perspectives | | | |
|---|---|---|---|
| Operator | Operator Assistant | Proctor | Observers |
| VR/with Controller or Haptic Glove/ Desktop | VR/with Controller or Haptic Glove/ Desktop | VR/with Controller or Haptic Glove/ Desktop | VR/Desktop |
| Virtual | | | |
| Virtual | | | |
| Virtual | | | |
| Virtual | | | |
| Virtual | | | |
| Virtual | | | |
| Virtual | | | |
| Virtual | | | |
| NA | | | |

Description of the perspective viewed by all parties involved in the basic communication product (contd.).

FIG. 3C

EXTENDED REALITY COMMUNICATIONS ENVIRONMENT

CROSS-REFERENCE TO RELATED APPLICATION

This application claims the benefit of priority of U.S. provisional application No. 63/380,740, filed Oct. 24, 2022, the contents of which are herein incorporated by reference.

BACKGROUND OF THE INVENTION

The present invention relates to extended reality communications environments and, more particularly, those utilized for communications between a proctor and an operator.

With the medical community, the introduction of virtual reality and augmented reality technologies has provided unique opportunities for expanding the capabilities of telemedicine used to interconnect medical providers located remotely from one another and patients. Telemedicine capabilities are utilized to provide medical education as well as assistance during medical procedures on patients.

One such system, offered by Proximie, includes a secure (HIPPA) cloud-based Augmented Reality (AR) platform that allows for the interaction of an operator with a proctor surgeon using a bird's eye camera view of the operation. The system includes AR enhancement of a video feed displayed on a computer monitor that is visible by the operator. The proctor uses the AR enhancement to annotate the video feed plus audio instructions to explain to the operator exactly how to proceed with the operation. The communication method is reported to be effective, helping to complete the surgical repair of an injured hand—See "Demonstration of the Effectiveness of Augmented Reality Telesurgery in Complex Hand Reconstruction in Gaza" from PRS Global Open, 2018.

While proctor annotations on a video feed of a surgical field proctor may provide improved guidance to a surgeon performing a procedure, the surgical environment presents many complexities. In many instances, the ability to assess and guide the performance of the procedure requires multiple sensory cues beyond those provided by a video presentation. Likewise, movements in a three-dimensional space remain difficult to demonstrate with two-dimensional annotations applied to the video presentation.

As can be seen, there is a need for an improved communications environments and, particularly, those utilized for communications between a proctor and an operator performing a procedure on a work object.

SUMMARY OF THE INVENTION

In one aspect of the present invention, an extended reality communications system is disclosed. The extended reality communications system includes an operator station comprising at least one of an operator augmented reality (AR) headset or an operator extended reality (XR) headset configured to be worn by an operator. A plurality of operator cameras are disposed in a spaced apart relation about the operator station and oriented to capture movements of the operator in a three-dimensional space of the operator station and to capture a three-dimensional representation of a work object. One or more operator tools are manipulable by the operator to perform a procedure on the work object.

A proctor station includes at least one of a proctor AR headset or a proctor virtual reality (VR) headset adapted to be worn by a proctor. A pair of haptic gloves are adapted to be worn by the proctor and are configured to capture movement information corresponding to a three-dimensional hand movement of the proctor. One or more virtual tools are provided corresponding to the one or more operator tools.

An operator computing device is communicatively coupled with the at least one of the operator AR headset or the operator XR headset, and the plurality of operator cameras. Likewise, a proctor computing device is communicatively coupled with the at least one of the proctor AR headset or the proctor VR headset and the pair of haptic gloves.

At least one server is communicatively coupled with each of the operator computing device and the proctor computing device. The server is configured to communicate the three-dimensional representation of the work object between the operator computing device and the proctor computing device and to communicate the three-dimensional hand movements of the proctor and the one or more virtual tools in a three-dimensional space of the proctor station between the proctor computing device and the operator computing device. A three-dimensional holographic representation of the work object is projected in a proctor field of view at the proctor station.

In some embodiments, a three-dimensional holographic representation of the three-dimensional hand movement of the proctor are projected in an operator field of view of the work object at the operator station. A three-dimensional holographic representation of the one or more virtual tools are projected in the operator field of view of the work object at the operator station.

In some embodiments, a three-dimensional holographic representation of the movements of the operator are projected in the proctor field of view of the work object at the proctor station.

In some embodiments, a LiDAR camera is configured to provide a three-dimensional holographic representation of one or more proctor work inputs on the work object.

In some embodiments, an operator headset camera is carried with the at least one of the operator AR headset or the operator XR headset. The operator headset camera is oriented with field of view of the operator. A proctor headset camera is carried with at least one of the proctor AR headset or the proctor VR headset. The proctor headset camera is oriented with the field of view of the proctor.

In some embodiments, a camera with an optical zoom as well as pan and tilt capabilities is operable by the proctor via a VR controller.

In other embodiments, a WebRTC server provides an audio and video communications channel between the proctor station and the operator station. A translator is configured to accommodate a language disparity between the proctor and the operator.

In other embodiments, a real-time dashboard that displays one or more vital signs relating to a procedure performed on the work object.

In yet other embodiments, a server database contains a data library defining a digital twin representation of the one or more operator tools.

In other aspects of the invention, a method of extended reality communications is disclosed. The method includes, comprising establishing, at a server, a dedicated server hosting a session of an extended reality communications network. The dedicated server interconnects an operator computing device and a proctor computing device. A three-dimensional representation of a work object captured by multiple three-dimensional depth cameras disposed in a spaced apart relation at an operator station is received at the server. The three-dimensional representation of the work object is transmitted by the server to a proctor computing device configured to project a three-dimensional holographic representation of the work object via at least one of a proctor augmented reality (AR) headset and a proctor virtual reality (VR) headset adapted to be worn by a proctor within a proctor station. A tracking of a pair of haptic gloves configured to be worn by the proctor to capture a proctor hand movement in a three-dimensional spatial relationship with the three-dimensional holographic representation of the work object are received at the server from the proctor computing device.

In some embodiments, the method includes transmitting, by the server, the tracking of the proctor hand movement to the operator computing device to project a three-dimensional holographic representation of the proctor hand movement in a three-dimensional relationship with the work object to at least one of an operator augmented reality (AR) headset or an operator extended reality (XR) headset configured to be worn by an operator.

In some embodiments, a three-dimensional representation of an operator station captured by the multiple three-dimensional depth cameras disposed at the operator station is received at the server. The server transmits the three-dimensional representation of the operator station to the proctor computing device to project the three-dimensional representation of the operator station in the at least one of the proctor augmented reality (AR) headset and the proctor virtual reality (VR) headset.

In some embodiments, the method includes receiving, at the server, a three-dimensional movement of a mirror work tool manipulated by the pair of haptic gloves in the spatial relationship with the three-dimensional holographic representation of the work object. The three-dimensional movement of the mirror work tool is transmitted by the server to the operator computing device to project the three-dimensional movement of the mirror work tool to one of the operator AR headset or the operator XR headset in a three-dimensional spatial relation with the work object.

In some embodiments, the method includes retrieving from a data library of a server database operatively connected with the server, at least one digital twin defining a three-dimensional representation of at least one of the one or more operator tools, or an operator equipment item located in the operator station. The server transmits at least one digital twin to the proctor computing device. The digital twin is projected as the mirror work tool.

In some embodiments, the method includes receiving, at the server, a three-dimensional location of the one or more equipment items captured by the multiple three-dimensional depth cameras of the operator station. The server spawns, from the data library, the digital twin of each of the one or more equipment items. The location of the digital twin is transmitted by the server to the proctor computing device to project a three-dimensional holographic representation of the digital twin to at least one of the operator AR headset or the operator XR headset at a corresponding three-dimensional location within the proctor station.

In some embodiments, the method includes detecting a movement of one or more of the equipment item and the work tool. When the movement is detected, the location of the one or more of the equipment item and the work tool are updated. The updated location is then recorded.

In some embodiments, the method includes receiving, at the server, a location of one or more physical calibration points in the operator station determined by the multiple three-dimensional cameras. A location of one or more virtual calibration points in the proctor station are received at the server, determined by a finger gesture of the proctor. A difference between the one or more physical calibration points and the one or more virtual calibration points is determined. When there is a difference, one or more of a translation and a rotation of the virtual representation of the three-dimensional holographic representation of the proctor station is performed to match the three-dimensional space of the operator station.

These and other features, aspects and advantages of the present invention will become better understood with reference to the following drawings, description and claims.

BRIEF DESCRIPTION OF THE DRAWINGS

FIG. 1A is a schematic diagram of a mixed virtual reality communications environment illustrating an active observer station and a proctor station.

FIG. 1D is a continuation of the schematic diagram of the mixed virtual reality communications environment showing communications with a server.

FIG. 3A is a table showing combinations of views for the operators, operator assistants, proctors, and observers when employing the extended reality communications system for a Real Situation.

FIG. 3B is a table showing combinations of views for the operators, operator assistants, proctors, and observers when employing the extended reality communications system for XR Training and/or Planning.

FIG. 3C is a table showing combinations of views for the operators, operator assistants, proctors, and observers when employing the extended reality communications system for Virtual Reality Training.

DETAILED DESCRIPTION OF THE INVENTION

Figure 1B:
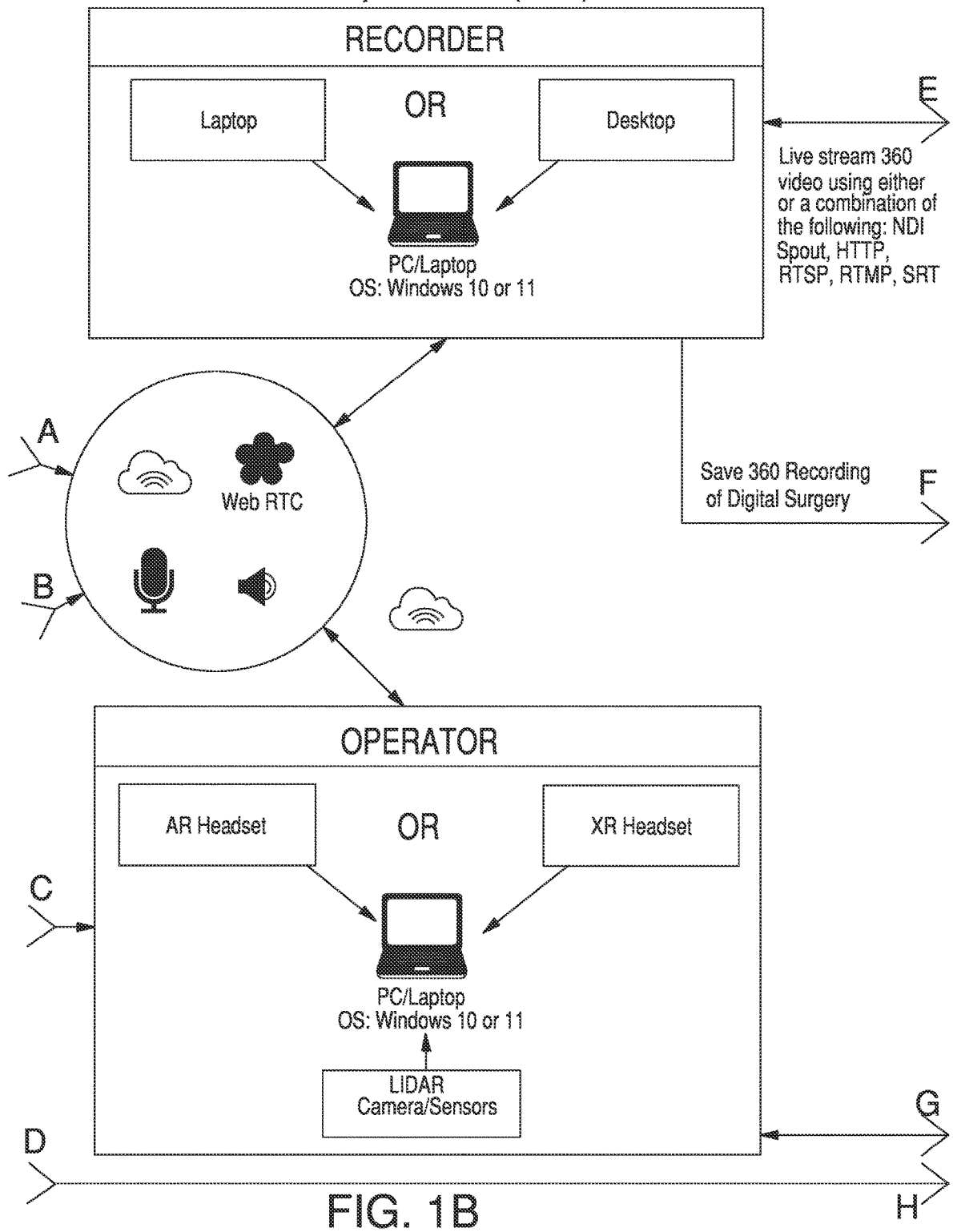
FIG. 1B is a continuation of the schematic diagram of the mixed virtual reality communications environment showing a recorder station, an operator station, and interconnections with a WebRTC server.
Figure 1C:
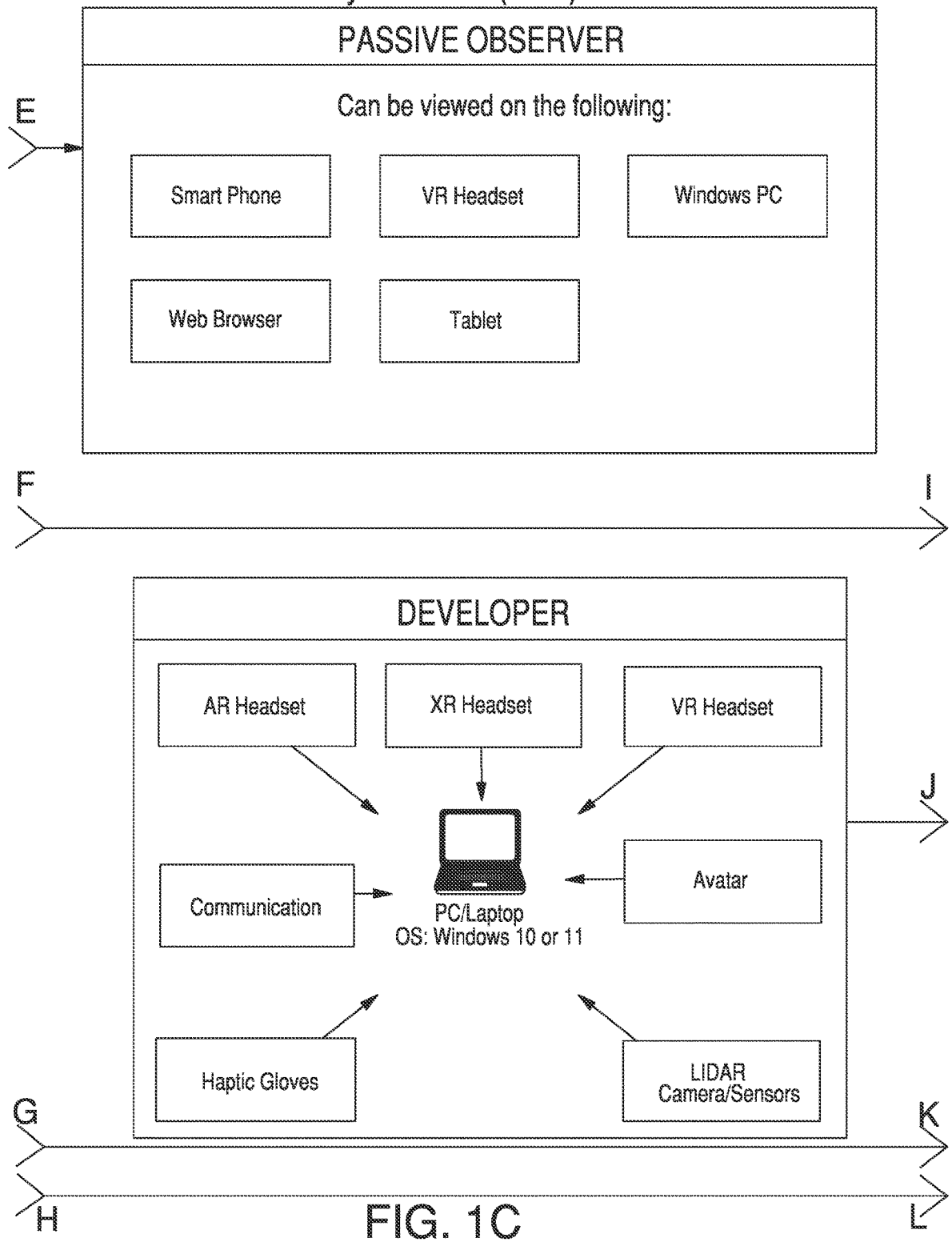
FIG. 1C is a continuation of the schematic diagram of the mixed virtual reality communications environment showing a passive observer station and a developer station.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, embodiments of the present invention provide an extended reality communications environment, system, method, and computer program product, hereinafter Veyond Metaverse. The Veyond Metaverse communication environment provides for remote real-time communications between a proctor and an operator, where the operator is performing tasks on a local work object. In representative embodiments of implementing the method, the proctor may, for example be a teaching surgeon, the operator may be one or more surgeons, or surgical students, and the work object may be a patient.

In a preferred embodiment, Veyond Metaverse provides the medical community with a communications platform that enables exact procedural details to be transmitted from one site to another through a mixed virtual reality environment. The Veyond Metaverse technology enables a "proctor" at a remote location to demonstrate to an "operator" exact procedural details and instructions throughout a procedure. In some embodiments, the exact procedural details are provided by casting a hologram of the proctor's hands, instruments, or other instructions directly on a patient, thereby instructing the operator to execute tasks exactly as described. The holographic projection allows the operator to maintain focus on the patient without the need to turn their head to consult another screen for instructions.

A proctor station, schematically shown in FIG. 1A allows the proctor to view the patient and the operator using a full virtual reality (VR) headset and communicates procedural details using haptic gloves and virtual instruments to manipulate holographic views cast onto the operator's field of view of the patient through an Extended Reality (XR) headset. Communication may be complimented with audio, text boxes, and a real-time dashboard that displays important information concerning vital signs and related information that's important for the specific procedure.

Veyond Metaverse uses a mixture of haptic, virtual keyboard, VR, XR, and audio inputs to provide more exact instructions between a proctor and an operator that are projected as a holographic image directly on a work object, such as a patient. A non-limiting embodiment of the Veyond Metaverse environment is shown in reference to FIGS. 1A-1D. In a basic configuration, the Veyond Metaverse environment includes a proctor station and an operator station communicatively coupled with one or more servers. Each of the proctor station and the operator station may be contained within an enclosure, such as a room. In the surgical setting for performing a surgical procedure on a patient, the operator station may include an operating room or a surgical suite.

The proctor station, schematically shown in FIG. 1A includes at least one XR headset or a VR headset, configured to be worn by the proctor. The proctor station also includes haptic gloves that are configured to be worn by the proctor. In the Veyond Metaverse environment, the haptic glove technology is utilized capture hand movements of the proctor to allow a three-dimensional holographic projection of the proctor's hand movements to be directly cast in the operator field of view onto the patient. Similarly, the pressure sensors feature of the haptic glove may also be used for the proctor to feel a pressure exerted by the operator during a therapeutic massage.

One or more web cameras may also be provided within the proctor station, the one or more web cameras oriented to capture movements of the proctor in a three-dimensional space within the proctor station. For example, the one or more web cameras may be used to locate and monitor the position of the proctors' hands, to augment the haptics signals of the haptic gloves, or in the case that the haptic gloves are not available or not found to be effective for a specific procedure.

The proctor station is also provided with audio communications, including a sound emitting device, such as a speaker or earphone, and a sound capture device, such as a microphone, for audio communications between the proctor station and the operator station. The audio channel may be further configured with a translator for real-time language translation of communications between the proctor and the operator accommodate for a language disparity between the proctor and the operator. Other modules may include a dictation module for dictation of the audio communications to text using an Artificial-Intelligence (AI) driven natural language processing tool.

Figure 2:
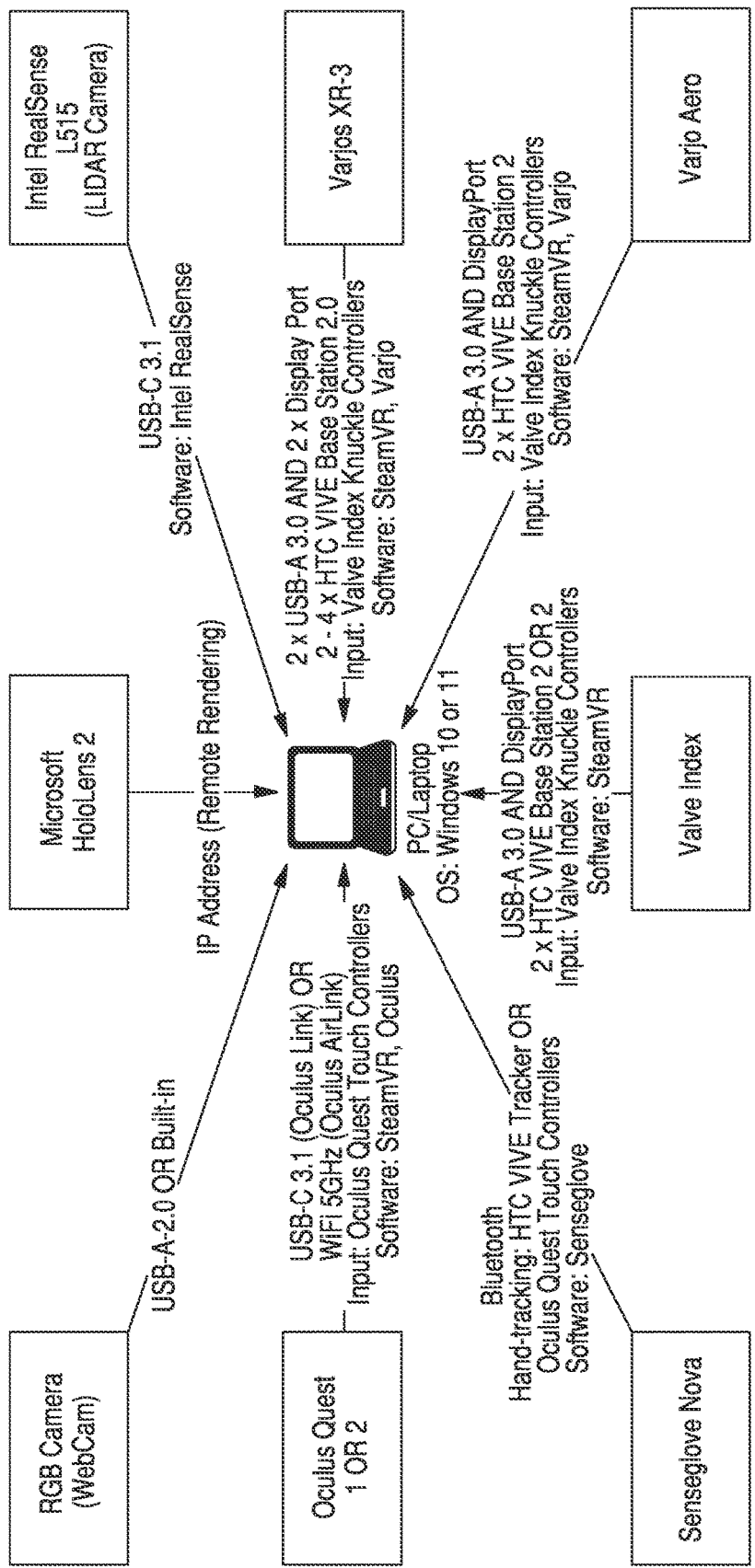
FIG. 2 is a view of representative components and communicative couplings for the active and passive observer station, recorder station, proctor station and operator stations.

The proctor station may be equipped with one or more mirror work tools, representing a matched set of one or more operator work tools present in the operator station. In the instance of the proctor station, the mirror work tools may be virtual representations, or digital twins, of the operator work tools. The proctor station may also include one or more handheld or remotely operable controllers configured for the proctor to control one or more equipment items in the operator station. Each of the XR/VR headset, haptic gloves, audio communications, and the one or more web cameras are communicatively coupled with a proctor computing system, such as a personal computer, laptop, or the like, associated with the proctor station. The communicative coupling may be by a direct connection, a wireless connection, or a combination thereof, such as illustrated in FIG. 2.

Virtual models, or digital twins, of all equipment used for a specific procedure are provided in a virtual cabinet, stored in a server database, and presented in the virtual operating room. Computer vision can be used to match the equipment in the real world to that present in the virtual world from a library created by VM and included in the cabinet.

The operator station, such as shown in FIG. 1B includes at least one of an AR headset or an XR headset configured to be worn by the operator. A work object support is included to carry the work object. One or more operator work tools are included for the operator to perform work on the work object. The one or more operator work tools are organized in a cabinet or a work tray. In the case where the work object is a patient, the work object support is an operating table. The one or more operator work tools include a surgical or an operating room instrument. When utilized as a training vehicle, the one or more work tools may also be digital twins of real work, such as surgical instruments, utilized for a particular procedure.

A plurality of cameras are disposed in a spaced apart relation about the operator station and are oriented to capture movements of the operator in three dimensions and to capture a three-dimensional representation of the work object. The plurality of cameras may include four types of cameras in the operators' workspace including a headset camera, a 3D camera, a 3D depth camera, and a camera with an optical zoom. The basic configuration preferably includes 5 overhead 3D depth cameras, one optical zoom camera, and the headset cameras in each of the proctor's and operators' headsets. The headset cameras are oriented to capture a field of focus of the operator and the proctor.

One or more of the plurality of cameras may be configured with a controllable magnification that is operable for targeted imaging of a work site on the work object. For example, the magnification allows the proctor to define an area of his field of view to magnify (define with a box) and magnify within the box with gesture inputs and two fingers. The magnified box can be relocated within the proctor's view, so it does not interfere with the original field of view.

Likewise, at least one of the plurality of cameras may include a 3D depth camera and associated sensors configured to provide a detailed three-dimensional holographic representation of one or more proctor work inputs on the work object. By way of non-limiting example, the 3D depth cameras may be a light detection and ranging, or laser imaging, detection and ranging (LiDAR) camera. The exact positions of each of the plurality of cameras within the operator station may be determined based on the optical characteristics and specifications provided with the specific model of the camera.

The operator station is also provided with audio communications including a sound emitting device, such as a speaker or earphone, and a sound capture device, such as a microphone, for audio communications between the proctor station and the operator station. The operator station may also be equipped with operator equipment items, such as instrumentation adapted to monitor one or more parameters of the work object. In the case of an operating room, the instrumentation may include one or more patient monitors, such as an EKG, blood pressure, respiratory monitors, saturated oxygen sensors, and the like, as best suited for the patient condition and the procedure to be performed by the operator. Likewise, the operator station may be outfitted with one or more work tools used by the operator to perform a procedure on the work object.

Each of the XR headset, the plurality of cameras, the audio communications, instrumentation, and work tools may be communicatively coupled with an operator computing system, such as a personal computer, laptop, or the like, associated with the operator station. The communicative coupling may be by a direct wired connection, a wireless connection, or a combination thereof.

Each of the proctor computing system and operator computing system are communicatively coupled with the server, via a network communication, such as the Internet. The server may include a plurality of servers, such as a dedicated server 1 and an application server 2. The server may also contain or provide access to a server database for storage and retrieval of data. As will be appreciated, the server and the server database may be implemented in a cloud environment.

FIG. 2 provides representative hardware associated with the one or more items contained within each of the proctor station and/or the operator station. FIG. 2 also provides representative communicative couplings for each of the items with the proctor computing system and the operator computing system. The representative hardware may include one or more RGB cameras, Microsoft HoloLens 2, available from Microsoft, Redmond, Washington, Intel RealSense L515, Varhi XR3 mixed reality headset, available from Varjo Tech USA HQ, Arlington, Virginia. The communicative couplings may include wired and wireless communications, including but not limited to USB, DisplayPort, Wi-Fi, and Bluetooth.

The haptics input gloves may be implemented with Index Knuckle Controllers, by Valve Corporation, Bellevue, Washington. The configuration typically includes multiple base stations for capturing movements of the haptic input gloves in the three-dimensional space of the proctor workstation. The base stations may be a Vive SteamVR base station, available from HTC Corporation, Taoyuan City 330, Taiwan. Other haptic input devices may include SenseGlove Nova, available from SenseGlove, Los Angeles, CA.

FIG. 2 provides representative examples of devices that may be used in the Veyond Metaverse environment. The present invention is not restricted to the use of these specific devices, but are they are presented to show the functionality and utility of the invention as illustrated through their use. As will be appreciated, the basic configuration described in the foregoing may be augmented at one or more of the proctor station or the operator station. For example, multiple proctors may be outfitted in one or more proctor stations to support a certain procedure. Likewise, multiple operators may be outfitted in the operator station to perform one or more aspects of a given procedure.

The controlling software that creates and controls the Veyond Metaverse environment will be run primarily on the server computer. The software is configured to create a mixed reality environment of virtual holograms and real world objects for the operator to view the proctors' instructions projected directly on the work object, such as the patient. Views generated by the server are described in the table of FIG. 3, including some number of observers. The exact views used will depend on the application of the communication system and the complexity of the procedure to be performed. Likewise, the configuration may depend on whether the communication system is being utilized in a real situation, such as operating on a patient, or is being utilized in a planning or a training environment.

As described previously, the proctor will have access to virtual tools of the operator tools. The virtual tools may be implemented as virtual tools that are a digital twin of the exact work tools, instrumentation, and devices that the operator will be using during the procedure. The digital twins may be presented as a holographic representations of instruments that function in a 3D virtual space as the originals do. For example, the proctor could pick up a digital twin of a pair of scissors and use these to demonstrate the cutting of a suture, tissue, or the like. All participants will view the hologram of the digital twin being used by the proctor on the work object. Similarly, the proctor can use his haptic gloves to indicate locations on the patient or pointing instruments to make positions more precisely known. A library of the digital twins are stored on the server database.

All views in the proctor and operator headsets may also be configured to include a dashboard that displays real time data generated by the instrumentation in the operator's space. The dashboard may include basic vital signs like blood pressure and EKC and any procedure specific measures, such as temperatures, pressures, etc.

The proctor and operator will have their choice of physical equipment, including eyewear, haptic gloves, etc. selected from devices previously validated by VM. For this reason, and since high-tech electronics are constantly being improved and updated, all equipment should be validated and verified before and during each session using an algorithm built into the program.

Figure 7:
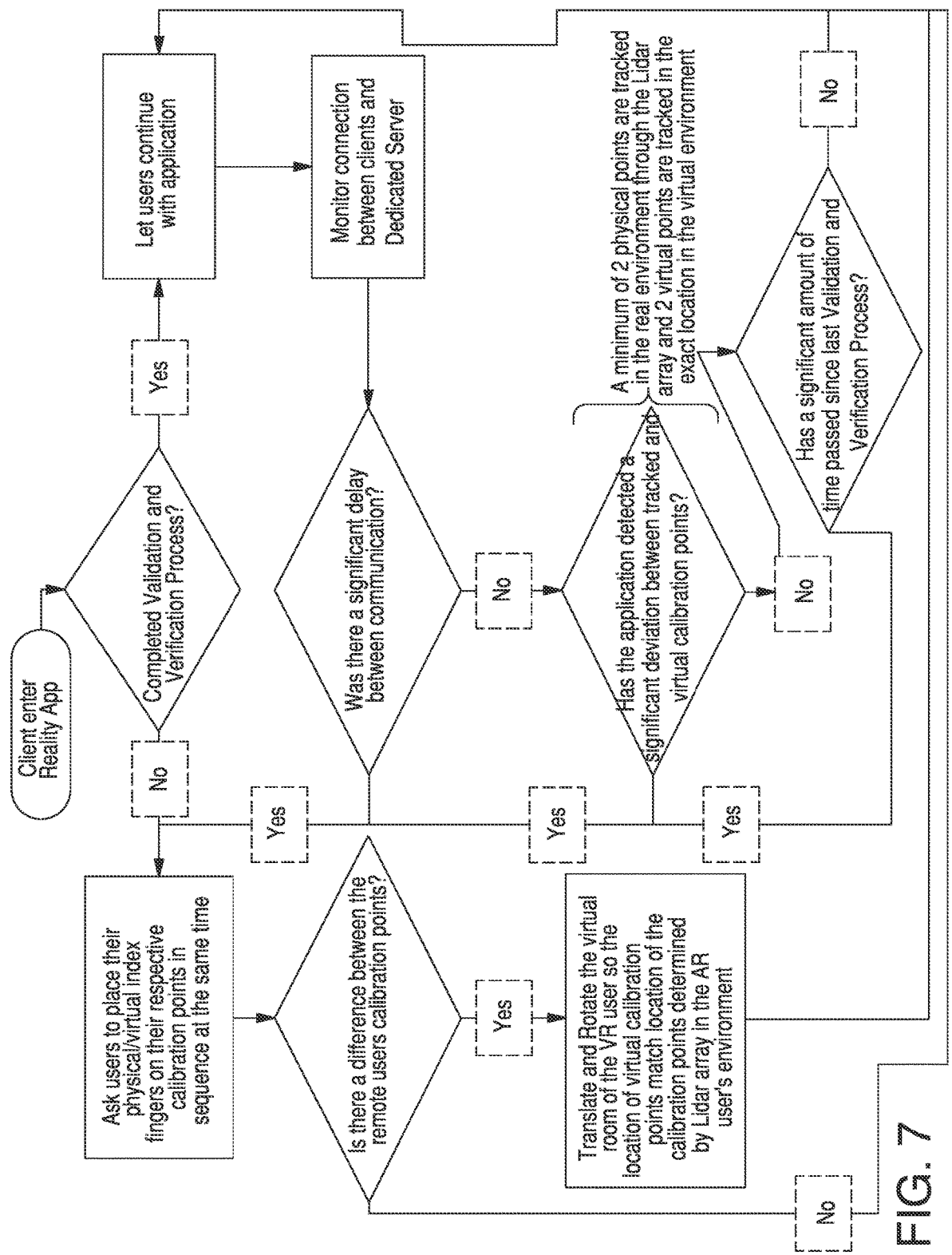
FIG. 7 is a flowchart showing a verification and validation process.

The Software-driven Validation and Verification (V&V) protocols, such as shown in FIG. 7, may include one or more of the following:

Measurement of overlaps of virtual and real images and confirmation that they are within a predetermined tolerance. Verify that the images don't shift with respect to one another during the procedure using instructions that popup during the procedure. Reference spots are to be uniquely identified.

Rendering time for images that are generated by the application need to be monitored and confirmed to be within predetermined tolerances throughout the protocol. A "Ping" signal from the headset, haptic gloves, or other devices may be used periodically to confirm temporal performance parameters. The time to process each rendered frame will also be monitored and tested against another predetermined tolerance.

Optimizing Communication throughout the procedure may be implemented by periodic measurements of "Ping" signals over various communications channels to determine an optimum communications speed. Once determined, the communications channel may be switched between satellite, 5G, LAN, and Internet communications channels.

Figure 4:
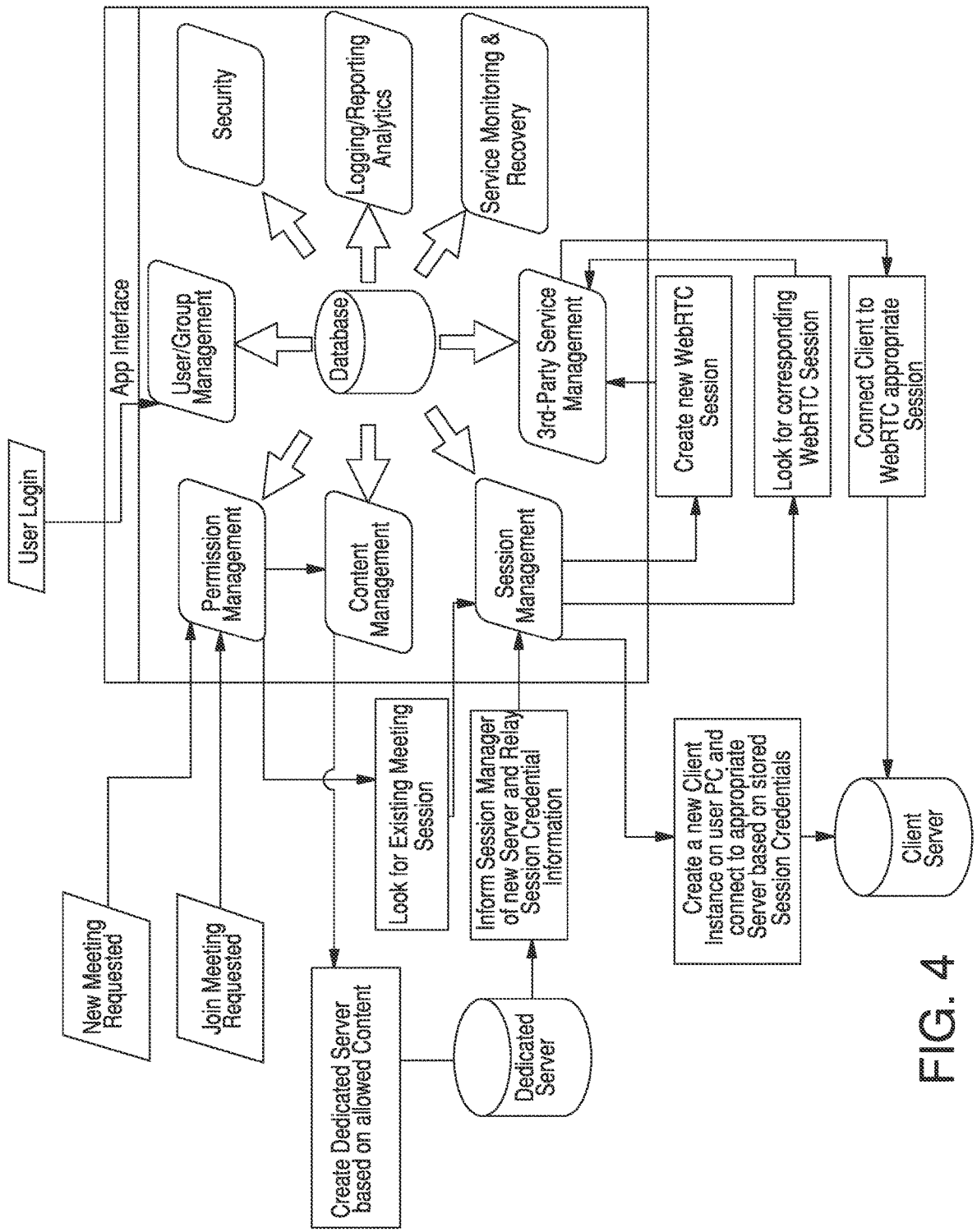
FIG. 4 is a schematic flow diagram showing interactions with an application interface.

A representative application interface is shown in reference to FIG. 4. A user login is processed by a user/group management module to confirm the credentials of the user. A security module, logging/reporting analytics module, and a service monitoring and recovery module may also be provided as components of the application interface.

A permissions management module manages requests for a new meeting or requests to join an existing meeting. When a new meeting is requested, a content management module creates a meeting instance by generation of a dedicated meeting server that is based on allowed content for that meeting. When the dedicated server is established, the dedicated server informs a session manager module of the dedicated server and relays session credential information to a session management module. The session management module then creates the new meeting session, as well as a new WebRTC session for voice and video communication. The session management module will also provide instructions to create a new client instance on the computing system of the user, such as the proctor computing system, or the operator computing system. The instructions allow a new client instance to connect the user's computing system to the corresponding dedicated server for the meeting. A $3^{rd}$-Party Service Management module provides management for each session corresponding to the new or an existing meeting hosted by the system.

When the permissions management module receives a request to join an existing meeting, the session management module is queried for the existence of the requested meeting. If the requested meeting exists, the session management module looks for the corresponding meeting session. The $3^{rd}$-party service management module joins the user to the requested session The session management module will also provide instructions to create a new client instance on the computing system of the user, such as the proctor computing system or the operator computing system. The instructions allow a new client instance to connect the user's computing system to the corresponding dedicated server for the meeting.

Figure 5:
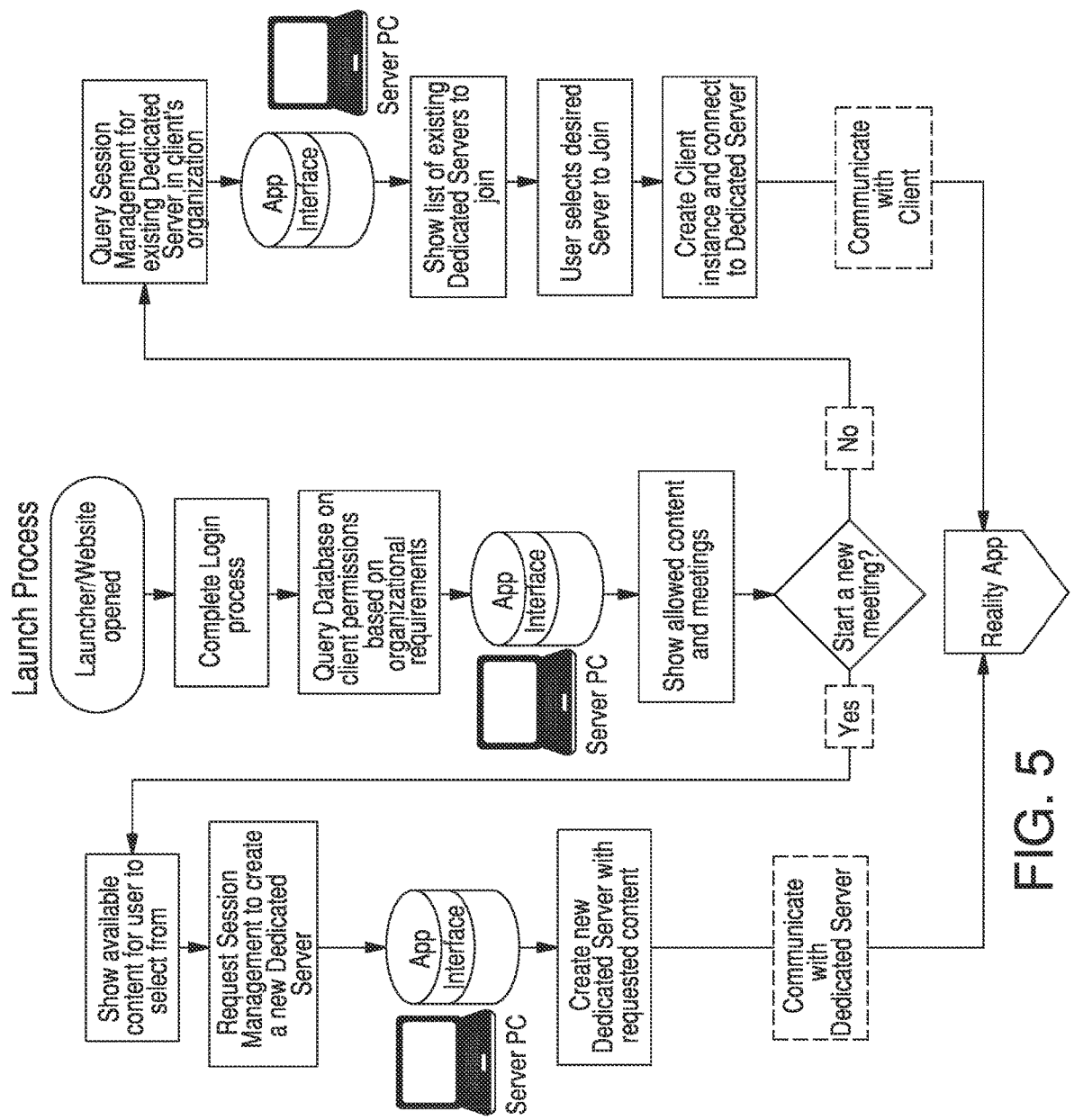
FIG. 5 is a flowchart showing a launch process.

A launch process, such as shown in FIG. 5, may be utilized to access and utilize the Veyond Metaverse communication system. During the launch process, an application launcher or website access is opened. The user completes a login process to provide their credentials for access to the system. The server database is queried via access through the application interface. The user may be presented a listing of allowed content and meetings, based on their credentials. The user is then prompted whether they would like to start a new meeting or join an existing meeting to which they have permissions.

If the user chooses to start a new meeting. The user is presented with choices for selecting available content for the meeting. When the user has selected the desired content for the meeting, the session management module creates the new dedicated server for the session, as previously described, and configures the user's computing device for communications with the dedicated server. The user then accesses and interacts withing the meeting via the reality application.

If the user chooses to join an existing meeting, the session management module is queried for the existing dedicated server for the meeting. The application interface shows a list of dedicated servers hosting an existing meeting to join. When the user selects a dedicated server hosting the desired existing meeting, a client instance is created on the user's computing device for connection to the corresponding dedicated server. The user then accesses and interacts within the meeting via the reality application.

Figure 6A:
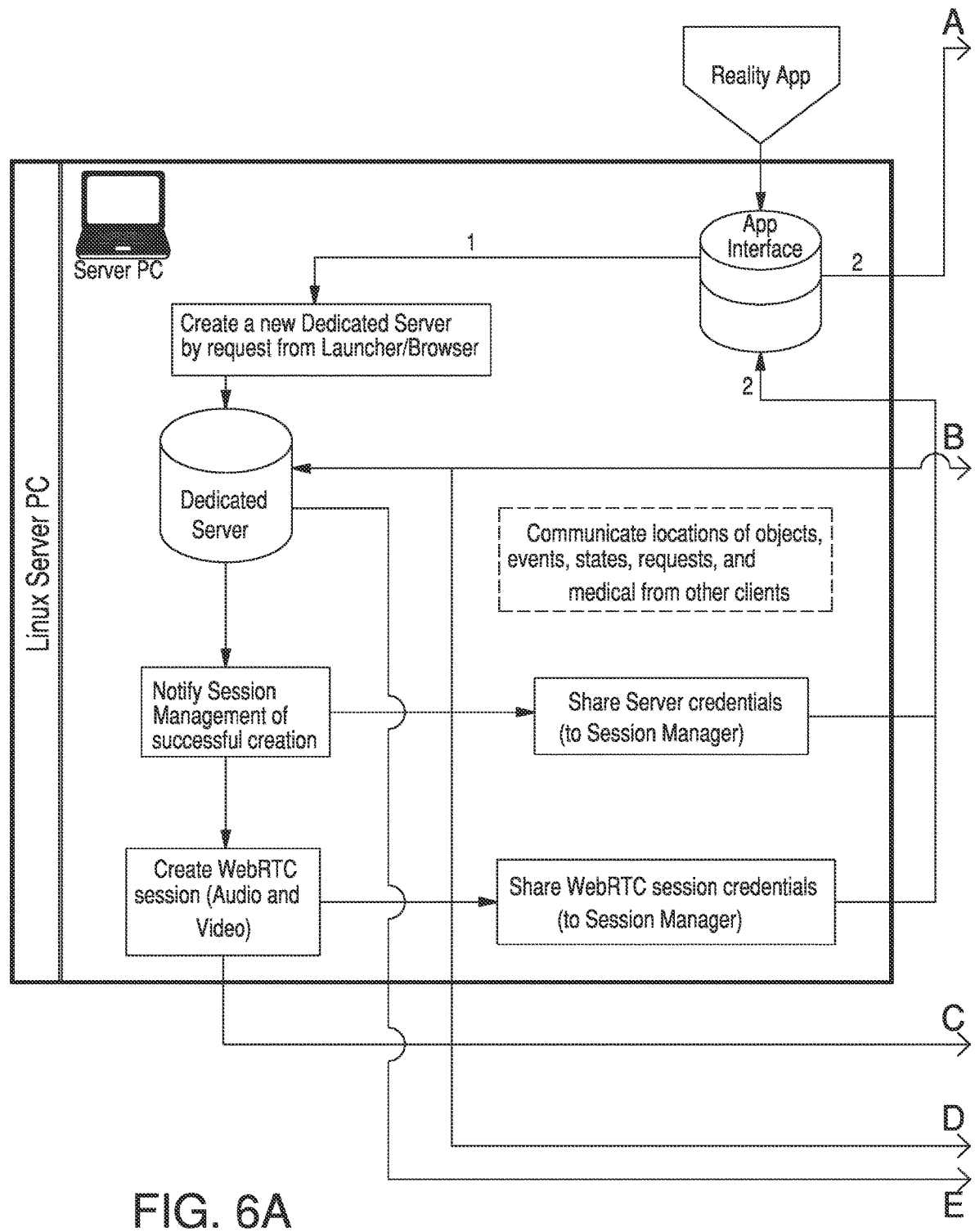
FIG. 6A is a flowchart illustrating the mixed virtual reality communications application processes.
Figure 6B:
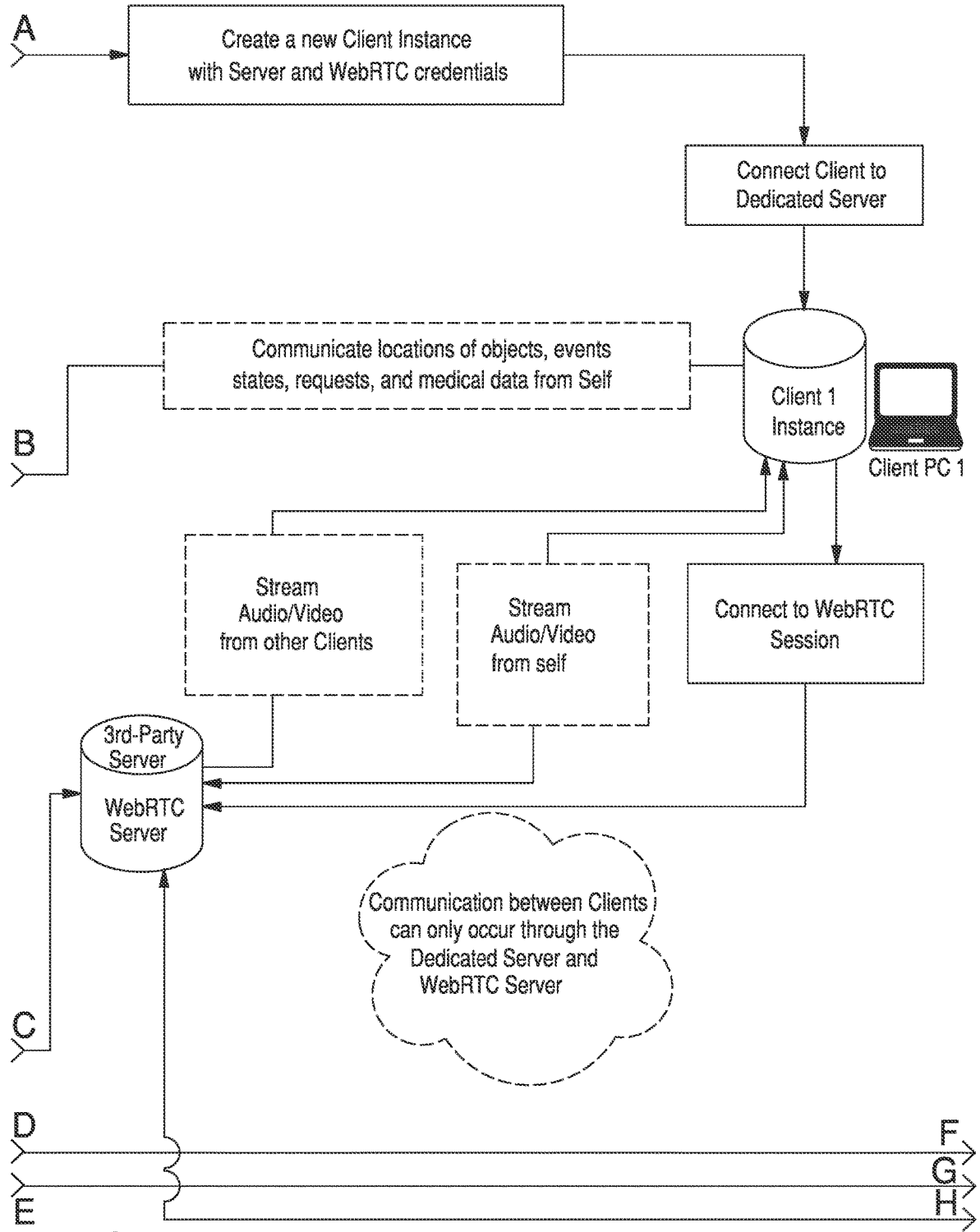
FIG. 6B is a continuation of the flowchart of FIG. 6A illustrating the mixed virtual reality communications application processes with a first client interface and a third-party Web RTC Server.
Figure 6C:
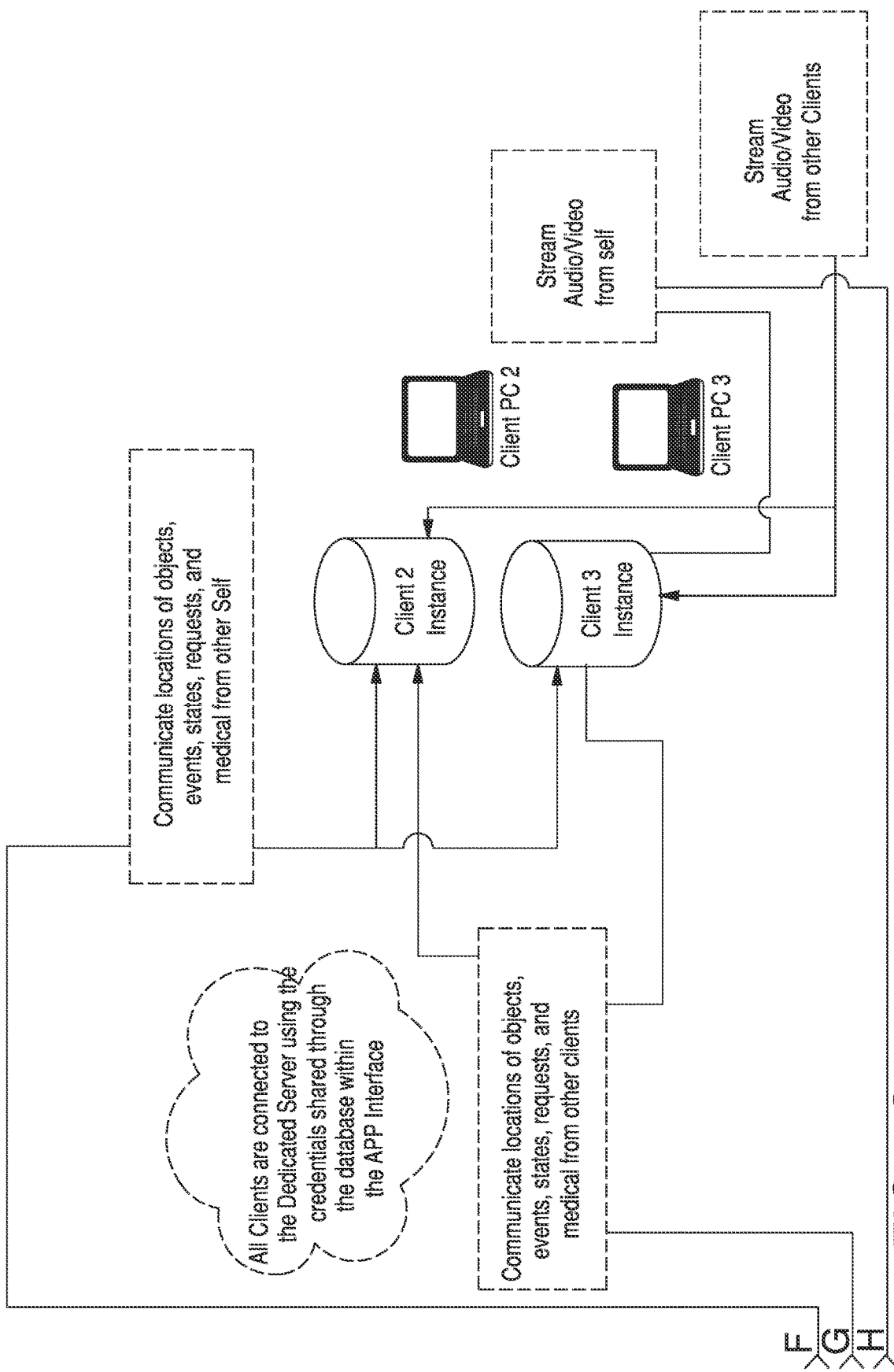
FIG. 6C is a continuation of the flowchart of FIGS. 6A and 6B illustrating the mixed virtual reality communications application processes with a second client interface and a third client.

Processes associated with the VR/XR reality application, hosted by the server are shown in reference to FIG. 6. As shown, the server creates the new dedicated server after receiving the request from the launcher. The dedicated server is configured to create the one or more client instances on each of the user computing devices. In the diagram shown, the one or more client instances include a client instance 1, a client instance 2, and a client instance 3. As will be appreciated from the present disclosure, any number of client instances, client 1 through client instance n may be initiated, based on system capabilities.

As previously described, the dedicated server notifies the session management module when the session is successfully created. Likewise, the session is created, as well as through WebRTC session, for communication of audio and video signals, which is shared via the session manager module.

Once the session is created, each client instance, client instance 1 through client instance n, stream the audio and video signals from their respective stations to the WebRTC server. The WebRTC server returns the streams from each of the other client instances to each client instance. Likewise, each client instance communicates locations of objects, events, states, requests, and medical data from their client instance to the dedicated server, which in turn communicates locations of objects, events, states, requests, and medical data from the dedicated server to each other client instance.

A verification and validation process is shown in FIG. 7. When a client enters the Veyond Metaverse application checks to determine whether a validation and verification (V&V) process has been completed. When no validation and verification process has been completed, the respective user is asked to place their physical and/or virtual index fingers on their respective calibration points in sequence and at the same time. The V&V process determines if there is a difference between the remote users' calibration points. When no difference is determined, the V&V process allows the users to continue with the application. When the V&V process detects a difference between the calibration points, the process translates and rotates the virtual room of the VR user, so the location of virtual calibration points matches the location of the calibration points determined by the 3D Depth Camera array in the AR user's environment to correct for the difference. The process then allows the users to continue with the application.

When a V&V process has been completed, the users are permitted to use the application. While using the application, the system monitors the connection between clients and the dedicated server. The V&V process determines whether there is a significant delay in communication according to a predetermined parameter. When a significant delay is detected, the users are prompted to complete the calibration process with their index fingers, as indicated above. When no significant delay is detected, the V&V process determines whether the application has detected a significant deviation between tracked and virtual calibration points. At least two physical points are tracked in the real environment through the 3D Depth Camera array and two virtual points are tracked in the corresponding location in the virtual environment.

When the application detects a significant deviation between the tracked and virtual calibration points, the users are prompted to execute the calibration procedure discussed above. When the application does not detect a significant deviation between the tracked and virtual calibration points, the V&V process determines if a significant amount of time, based on a predetermined temporal parameter, has passed since a previous V&V process. When the predetermined temporal parameter has been exceeded, the users are prompted to complete the calibration procedure described above. When the predetermined temporal parameter has not been exceeded, the V&V process allows the users to continue using the application.

Figure 8:
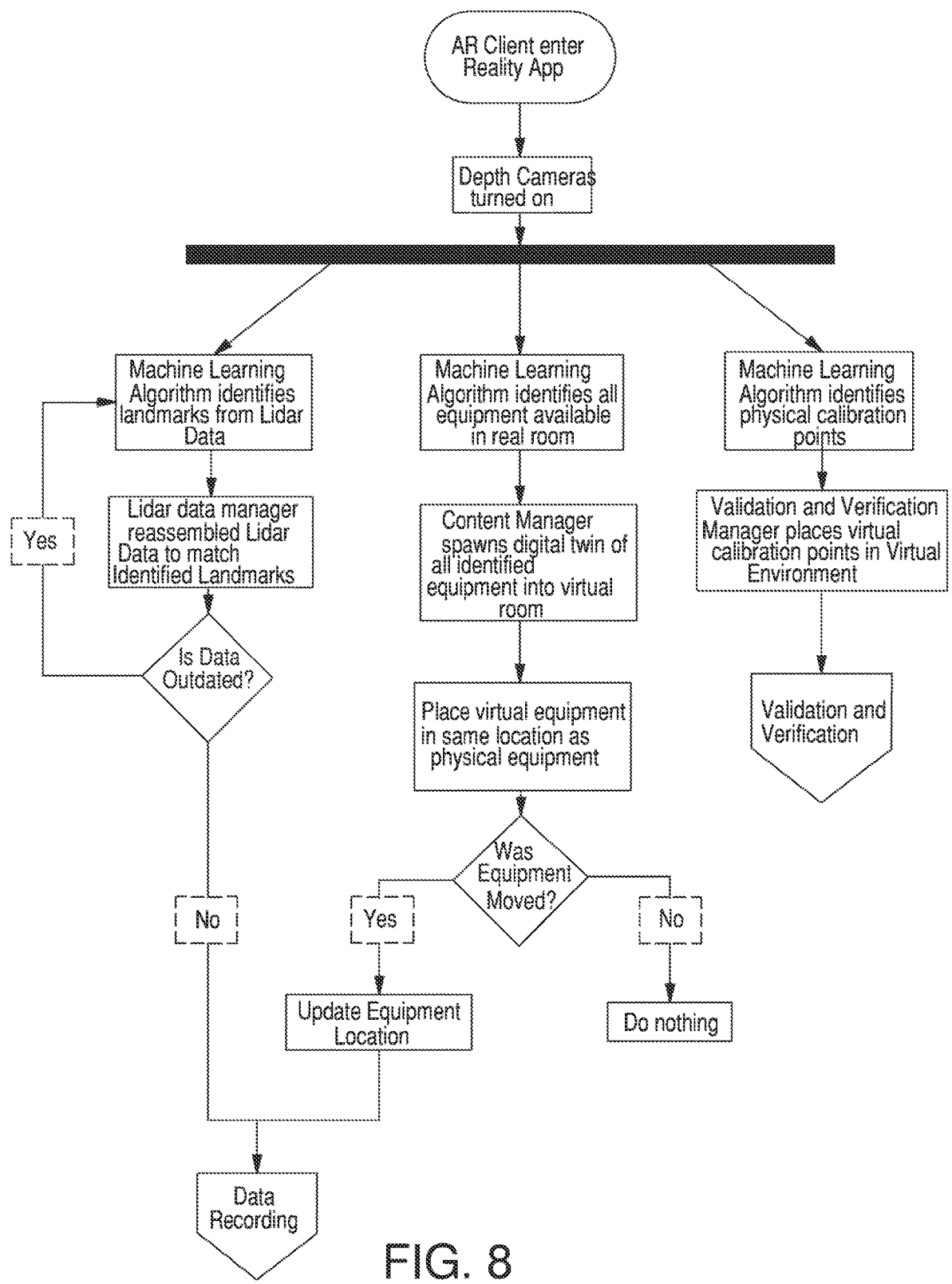
FIG. 8 is a flowchart showing an Augmented Reality Client entering the Reality Application and Reality Application processes.

An AR Client entry to the Veyond Metaverse app is shown in reference to FIG. 8. When an AR client enters the Veyond Metaverse app, the 3D Depth camera(s) are turned on. In one process a machine learning algorithm determines one or more landmarks from 3D Depth data. A 3D Depth data manager reassembles the 3D Depth data to match the one or more identified landmarks. The process determines whether the 3D Depth data is outdated. When the 3D Depth is outdated, the landmark process repeats. When the 3D Depth is not outdated, a data recording process is executed.

The 3D Depth process may also identify all equipment available in the operator station. The content manager spawns a digital twin of all identified equipment into the virtual room of the proctor station. The digital twin is placed in the corresponding location in the proctor station as the identified equipment of the operator station. The process then determines a movement of one or more equipment items. When a movement is detected, the location of the equipment item is updated. The equipment item location is then updated for data recording. If the location of the equipment item is not changed, do nothing.

The 3D Depth process may also identify physical calibration points. In this process a machine learning algorithm identifies one or more physical calibration points in the operator station. The validation and verification manager places a corresponding one or more calibration points in the virtual environment of the proctor station. The process then executes the validation and verification process, as previously described.

Figure 9:
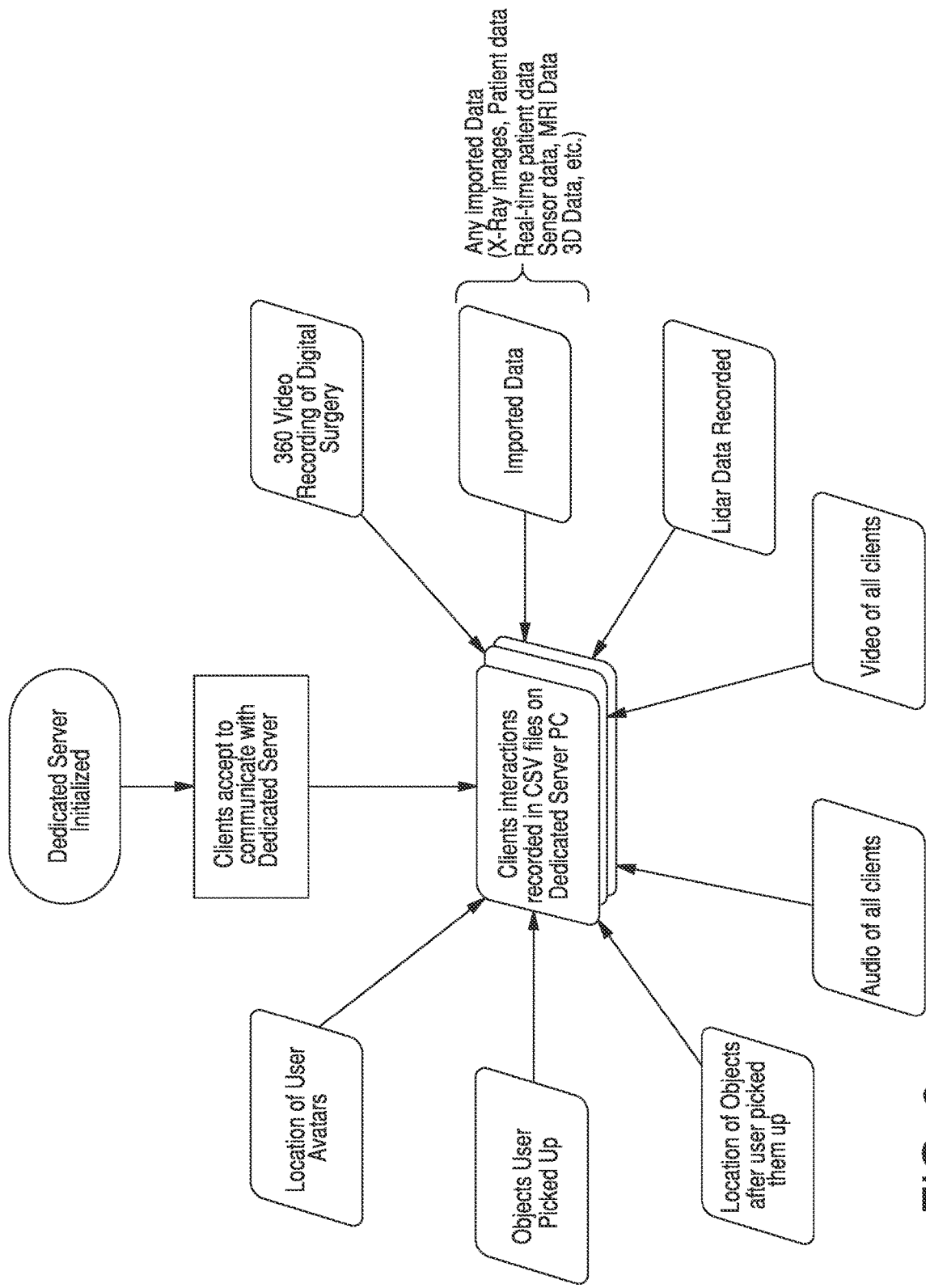
FIG. 9 is a flowchart showing a data recording process for the extended reality communications system.

A data recording process is shown in reference to FIG. 9. The process begins with the initialization of the dedicated server. When the client accepts communication with the dedicated server, one or more client interactions are recorded in a data repository connected with the dedicated server. In the non-limiting embodiment shown, the one or more client interactions are recorded in a comma separated variable (CSV) file, though any suitable data file format may be utilized.

The one or more client interactions may include: a location of a user's avatar; a 360 Video Recording of the Digital Surgery; objects a user picks up; a location of the objects after a user has picked up the object; an audio feed of all clients; a video feed of all clients; 3D Depth data that is recorded; and one or more models imported into the communication environment.

A recorder station may be provided as a built-in system within the software solution that records and streams a 360-degree view of the virtual environment giving the view from the recorder station. The recording may be streamed to a secondary viewing software that will allow passive observers to view the digital surgery on any device that at least supports a web browser. The 360-degree video recorded by the software will also be saved and uploaded from the recorder station for later viewing.

The system of the present invention may include at least one computer with a user interface. The computer may include any computer including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the software via the web browser using the internet, extranet, intranet, host server, internet cloud and the like.

The computer-based data processing system and method described above is for purposes of example only, and may be implemented in any type of computer system or programming or processing environment, or in a computer program, alone or in conjunction with hardware.

The present invention may also be implemented in software stored on a non-transitory computer-readable medium and executed as a computer program on a general purpose or special purpose computer. For clarity, only those aspects of the system germane to the invention are described, and product details well known in the art are omitted. For the same reason, the computer hardware is not described in further detail.

It should thus be understood that the invention is not limited to any specific computer language, program, or computer. It is further contemplated that the present invention may be run on a stand-alone computer system, or may be run from a server computer system that can be accessed by a plurality of client computing systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention and that modifications may be made without departing from the spirit and scope of the invention as set forth herein.

We claim:

1. A method of extended reality communications, comprising:

establishing, at a server, a dedicated server hosting a session of an extended reality communications network, the dedicated server interconnecting an operator computing device and a proctor computing device;

receiving, at the server, a three-dimensional representation of a work object captured by multiple three-dimensional cameras disposed in a spaced apart relation at an operator station;

transmitting, by the server, the three-dimensional representation of the work object to a proctor computing device configured to project a three-dimensional holographic representation of the work object via at least one of a proctor augmented reality (AR) headset and a proctor virtual reality (VR) headset adapted to be worn by a proctor within a proctor station;

receiving, from the proctor computing device, a tracking of a pair of haptic gloves configured to be worn by the proctor to capture a proctor hand movement in a three-dimensional spatial relationship with the three-dimensional holographic representation of the work object transmitting, by the server, the tracking of the proctor hand movement to the operator computing device to project a three-dimensional holographic representation of the proctor hand movement in a three-dimensional relationship with the work object to at least one of an operator augmented reality (AR) headset or an operator extended reality (XR) headset configured to be worn by an operator;

receiving, at the server, a three-dimensional movement of a mirror work tool manipulated by the pair of haptic gloves in the three-dimensional spatial relationship with the three-dimensional holographic representation of the work object;

transmitting, by the server, the three-dimensional movement of the mirror work tool to the operator computing device to project the three-dimensional movement of the mirror work tool to one of the operator AR headset or the operator XR headset in a three-dimensional spatial relation with the work object;

retrieving from a data library of a server database operatively connected with the server, at least one digital twin defining a three-dimensional representation of at least one of the one or more operator tools, or an operator equipment item located in the operator station;

transmitting, by the server, the at least one digital twin to the proctor computing device;

projecting the digital twin as the mirror work tool;

receiving, at the server, a three-dimensional location of the one or more equipment items captured by the multiple three-dimensional cameras of the operator station;

spawning, from the data library, the digital twin of each of the one or more equipment items; and transmitting, by the server, the location of the digital twin to the proctor computing device to project a three-dimensional holographic representation of the digital twin to at least one of the operator AR headset or the operator XR headset at a corresponding three-dimensional location within the proctor station.

2. The method of claim 1, further comprising:

receiving, at the server, a three-dimensional representation of an operator station captured by the multiple three-dimensional cameras disposed at the operator station; and transmitting, by the server, the three-dimensional representation of the operator station to the proctor computing device to project the three-dimensional representation of the operator station in the at least one of the proctor augmented reality (AR) headset and the proctor virtual reality (VR) headset.

3. The method of claim 2, further comprising:

receiving, at the server, a location of one or more physical calibration points in the operator station determined by the multiple three-dimensional cameras;

receiving, at the server, a location of one or more virtual calibration points in the proctor station, determined by a finger gesture of the proctor;

determining a difference between the one or more physical calibration points and the one or more virtual calibration points; and when there is a difference, performing one or more of a translation and a rotation of the three-dimensional holographic representation of the proctor station to match the three-dimensional representation of the operator station.

4. The method of claim 1, further comprising:

detecting a movement of one or more of the equipment item and the work tool; and when the movement is detected, update the location of the one or more of the equipment items and the work tool.

5. The method of claim 4, further comprising:

recording the updated location.

* * * * *